United States Patent [19]
Patel et al.

[11] Patent Number: 5,958,900
[45] Date of Patent: Sep. 28, 1999

[54] USE OF ORGANOBORON COMPOUNDS AS ANTIFOULING AGENTS

[75] Inventors: Bomi Pilloo Patel, Mumbai, India; Mark A. J. Van der Flaas; Jef F. E. Van Gestel, both of Vosselaar, Belgium

[73] Assignee: American Cyanamid Company, Madison, N.J.

[21] Appl. No.: 08/854,215

[22] Filed: May 9, 1997

Related U.S. Application Data

[60] Provisional application No. 60/017,561, May 13, 1996.

[51] Int. Cl.$^6$ ..................................................... A01N 55/08
[52] U.S. Cl. .............................................. 514/64; 504/153
[58] Field of Search ................................. 514/64; 504/153

[56] References Cited

U.S. PATENT DOCUMENTS

| | | | |
|---|---|---|---|
| 4,983,589 | 1/1991 | Tsang et al. | 514/64 |
| 5,091,377 | 2/1992 | Tsang et al. | 514/63 |
| 5,354,740 | 10/1994 | Patel | 514/64 |
| 5,354,741 | 10/1994 | Patel | 514/64 |

*Primary Examiner*—Allen J. Robinson
*Attorney, Agent, or Firm*—Gregory M. Hill

[57] ABSTRACT

There is provided a method for controlling or combatting the attachment of a fouling organism to an underwater surface which comprises contacting said organism with an antifouling-effective amount of a diarylboron compound of formula I. A method for protecting aquatic structures against fouling by a marine or freshwater fouling organism and antifoulant compositions therefor are also provided.

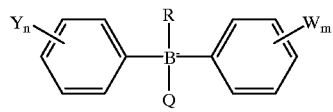

(I)

14 Claims, No Drawings

USE OF ORGANOBORON COMPOUNDS AS ANTIFOULING AGENTS

This application claims benefit of U.S. Provisional (Application) No. 60/017,561, filed May 13, 1996.

BACKGROUND OF THE INVENTION

The ever recurring growth of fouling organisms on underwater structures such as ships, docks, piers, pilings, fishnets, heat exchangers, dams, piping structures, intake screens, cooling towers and the like is a costly and hazardous problem in both marine and freshwater endeavors. The presence of fouling organisms such as barnacles, zebra mussels, algae, diatoms, hydroids, bryozoa, ascidians, tubeworms, Asiatic clams and the like can weigh down aquatic structures, hamper their hydrodynamics, reduce operating efficiency, increase susceptibility to corrosion, cause degradation and structural fractures, block or hamper water flow and water exchange and the like. A common method of controlling the presence or attachment of fouling organisms is to coat or permeate the underwater structure with a composition which comprises a toxic metal-containing compound such as tri-n-butyl tin or cuprous oxide. Although said compositions are somewhat efficacious antifoulants, they degrade slowly in aquatic environments and are, therefore, ecologically harmful.

Diarylboron compounds are known to be effective insecticidal, acaricidal and fungicidal agents useful in crop protection; said diarylboron compounds are described in U.S. Pat. Nos. 5,354,740, 5,354,741, 4,983,589 and 5,091,377.

It is an object of this invention to provide an environmentally and ecologically sound method of combatting or controlling marine and freshwater fouling organisms.

It is another object of this invention to provide an effective method for protecting aquatic structures against fouling by marine or freshwater fouling organisms.

It is a further object of this invention to provide antifoulant compositions which comprise diarylboron compounds as the active agents.

It is a feature of this invention that the antifouling methods and compositions are free of heavy metal complexes.

These and other features and objects of the invention will become more apparent from the detailed description set forth hereinbelow.

SUMMARY OF THE INVENTION

The present invention provides a method for controlling or combatting a marine or freshwater fouling organism which comprises contacting said organism or the locus thereof with an antifouling-effective amount of a diarylboron compound of formula I

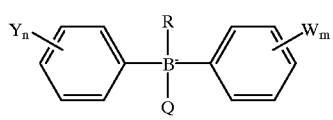
(I)

wherein R is $C_1$–$C_8$alkyl, $C_2$–$C_8$alkenyl or $C_2$–$C_8$alkynyl;
W and Y are each independently halogen, $C_1$–$C_8$alkyl or $C_1$–$C_8$haloalkyl;
m and n are each independently 0 or an integer of 1, 2 or 3;
Q is

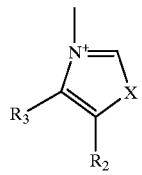 or 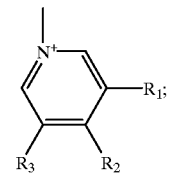

X is $NR_4$ or S;
$R_1$ is H, halogen, $C_1$–$C_8$alkyl, or $C_2$–$C_8$alkenyl;
$R_2$ and $R_3$ are each independently H, $C_1$–$C_8$alkyl, $C_1$–$C_8$haloalkyl, $C_1$–$C_8$alkoxy, $C_1$–$C_8$haloalkoxy, halogen, CN, $NO_2$, $COR_5$ or phenyl optionally substituted with one to three halogen or $NR_6R_7$ groups or $R_1$ and $R_2$ may be taken together with the atoms to which they are attached to form a saturated or unsaturated 6-membered carbocyclic ring optionally substituted with one to three halogen, $NO_2$, $C_1$–$C_4$alkyl or $C_1$–$C_4$alkoxy groups;
$R_4$ is $C_1$–$C_8$alkyl, $C_2$–$C_8$alkenyl or phenyl; and
$R_5$, $R_6$ and $R_7$ are each independently H or $C_1$–$C_4$alkyl.

The present invention also provides a method for the protection of aquatic structures against fouling by a marine or freshwater fouling organism and an antifoulant composition suitable for use therefor.

DETAILED DESCRIPTION OF THE INVENTION

Controlling or combatting fouling organisms in aquatic environments without harming beneficial species or threatening the ecological balance of said environment is a continuing scientific challenge. It has now been found that particularly effective antifouling agents are those diarylboron compounds of formula I

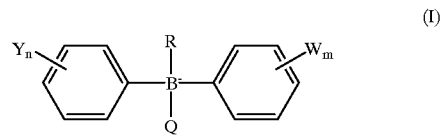
(I)

wherein R is $C_1$–$C_8$alkyl, $C_2$–$C_8$alkenyl or $C_2$–$C_5$alkynyl;
W and Y are each independently halogen, $C_1$–$C_8$alkyl or $C_1$–$C_8$haloalkyl;
m and n are each independently 0 or an integer of 1, 2 or 3;
Q is

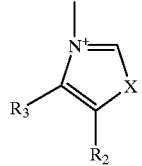 or 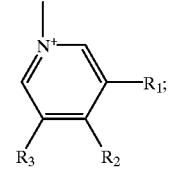

X is $NR_4$ or S; $R_1$ is H, halogen, $C_1$–$C_8$alkyl, or $C_2$–$C_8$alkenyl;
$R_2$ and $R_3$ are each independently H, $C_1$–$C_8$alkyl, $C_1$–$C_8$haloalkyl, $C_1$–$C_8$alkoxy, $C_1$–$C_8$haloalkoxy, halogen, CN, $NO_2$, $COR_5$ or phenyl optionally substituted with one to three halogen or $NR_6R_7$ groups or $R_1$ and $R_2$ may be taken together with the atoms to which they are attached to form a saturated or unsaturated 6-membered carbocyclic ring optionally substituted with one to three halogen, $NO_2$, $C_1$–$C_4$alkyl or $C_1$–$C_4$alkoxy groups;

$R_4$ is $C_1$–$C_8$alkyl, $C_2$–$C_8$alkenyl or phenyl; and
$R_5$, $R_6$ and $R_7$ are each independently H or $C_1$–$C_4$alkyl.

Preferred antifoulant agents suitable for use in the methods and composition of the invention are those diarylboron compounds of formula I wherein R is $C_1$–$C_4$alkyl or $C_2$–$C_4$alkenyl; X is $NR_4$; m and n are 0; $R_4$ is $C_1$–$C_4$alkyl or $C_2$–$C_4$alkenyl; $R_2$ is hydrogen, halogen, $C_1$–$C_4$alkyl or phenyl; and $R_3$ is hydrogen or methyl.

In the specification and claims the term halogen designates Cl, Br, I or F and the term haloalkyl designates any alkyl group $C_nH_{2n+1}$ having from 1 halogen atom to 2n+1 halogen atoms wherein the halogen atoms are the same or different. Similarly haloalkoxy designates an $OC_nH_{2n+1}$ group having from 1 halogen atom to 2n+1 halogen atoms wherein the halogen atoms are the same or different.

Among the diarylboron compounds suitable for use in the methods and composition of the invention are:
(3-vinylimidazolinio)vinyldiphenylboron;
(3-methylpyridinio)methyldiphenylboron;
(4-phenylpyridinio)methyldiphenylboron;
(4-isopropylpyridinio)methyldiphenylboron;
(4-t-butylpyridinio)methyldiphenylboron;
(3-isopropylimidazolinio)vinyldiphenylboron;
(thiazolinio)methyldiphenylboron;
(5,6,7,8-tetrahydroisoquinolinio)methyldiphenylboron;
(isoquinolinio)methyldiphenylboron;
(3-bromopyridinio)methyldiphenylboron;
(4-acetylpyridinio)methyldiphenylboron;
(4-cyanopyridinio)methyldiphenylboron; and
(3-bromoisoquinolinio)methyldiphenylboron.

Said formula I diarylboron compounds and methods to prepare same are described in U.S. Pat. Nos. 5,354,740, 5,091,377 and 4,983,589.

A fouling organism which may be combatted or controlled by the method of the invention can be any marine or freshwater organism which can attach to an inner or outer surface of a structure which is submerged or in continual contact with water. Exemplary organisms include algae, including members of the phyla Chlorophyta and Phaeophyta, microbes, tunicates, including members of the class Ascidiacea, such as *Ciona intestinalis, Diplosoma listerianium*, and *Botryllus sclosseri*, members of the class Hydrozoa, including *Clava squamata, Hydractinia echinata, Obelia geniculata*, and *Tubularia larnyx*, bivalves, including *Mytilus edulis, Crassostrea virginica, Ostrea edulis, Ostrea chilensia*, and *Lasaea rubra*, bryozoans, including *Ectra pilosa, Bugula neritinia*, and *Bowerbankia gracilis*, polychaete worms, including *Hydroides norvegica*, sponges and members of the class Cirripedia (barnacles), such as *Balanus amphitrite, Lepas anatifera, Balanus balanus, Balanus balanoides, Balanus hameri, Balanus crenatus, Balanus improvisus, Balanus galeatus*, and *Balanus eburneus*. Organisms of the genus Balanus are frequent foulers of aquatic structures. Specific fouling organisms to which this invention is especially directed include barnacles, zebra mussels, algae, diatoms, hydroids, bryozoa, ascidians, tube worms and Asiatic clams.

Among the aquatic structures which may be protected by the method of invention are any submerged or partially submerged structure, either mobile or stationary, such as a fishnet, boat, ship, piling, pier, cooling tower, pipeline, standpipe, heat exchanger, dam, intake screen or the like.

In actual practice the antifouling diarylboron compound may be brought into contact with a fouling organism by: a) coating the aquatic structure to be protected with an antifouling-effective amount of said diarylboron compound such that the antifouling compound is released into the aquatic environment immediately adjacent the external surface of said structure, b) including an antifouling-effective amount of the diarylboron compound within material formed into an aquatic structure which then releases said compound, c) releasing an antifouling-effective amount of said compound directly into the aquatic environment surrounding the structure to be protected, or d) any other method wherein the diarylboron compound comes in contact with the fouling organism.

The amount of diarylboron compound to be used in the method of invention will vary according to the specific compound used, the identity of the fouling organism to be controlled, degree of infestation of the surrounding aquatic environment, the water temperature, the mode of contact and the like.

Compositions of the invention comprise an aquatically acceptable inert carrier and an antifouling-effective amount of a diarylboron compound of formula I. For application onto structural surfaces, preferred compositions of the invention include a film-forming component such as a polymer resin solution. Exemplary polymer resins include unsaturated polyester resins formed from: a) unsaturated acids or anhydrides, such as maleic anhydride, fumaric acid, itaconic acid and the like; b) saturated acids or anhydrides, such as phthalic anhydride, isophthalic anhydride, terephthalic anhydride, tetrahydrophthalic anhydride, tetrahalophthalic anhydride, chlorendic acid, adipic acid, subacic acid, and the like; c) glycols, such as ethylene glycol, 1,2 propylene glycol, dibromoneo-pentyl glycol, and the like; or d) vinyl monomers, such as styrene, vinyl toluene, chlorostyrene, bromostyrene, methylmethacrylate, ethylene glycol dimethacrylate and the like. Other suitable resins include vinyl ester-, vinyl acetate-, and vinyl chloride-based resins, elastomeric components, vulcanized rubbers, and urethane-based resins.

In order to present a more clear understanding of the invention, specific examples thereof are set forth below. These examples are merely illustrative and are not to be understood as limiting the scope and underlying principles of the invention in any way. Indeed, various modifications of the invention, in addition to those shown and described herein, will become apparent to those skilled in the art from the following examples and the foregoing description. Such modifications are also intended to fall within the scope of the appended claims.

EXAMPLE 1

Evaluation Of Marine Antifouling Activity Of Test Compounds

The crustaceous marine animal *Artemia salina* is used as a model organism for other marine animal foulers (e.g. barnacles) in this laboratory assay. Test compounds are dissolved in dimethylsulfoxide at a concentration of 4,000 ppm, diluted to a concentration of 200 ppm with water and further diluted with Probst artificial seawater to a concentration of 10 ppm. Approximately 30 *Artemia salina* instar II larvae are incubated in microwell plates in 2 ml of Probst artificial seawater containing 10 ppm of the test compound. Survival of the organism is evaluated after 24 hours, and test compounds are rated according to the scale shown below. Test results are shown in Table I.

| RATING SCALE | |
| --- | --- |
| Rating | Definition |
| 1 | No activity, 0%–<20% mortality |
| 2 | Toxic effect, 20%–80% mortality |
| 3 | Completely active, >80% mortality |

TABLE I

| Test Compound | Art[1] |
| --- | --- |
| (3-vinylimidazolinio)vinyldiphenylboron | 3 |
| (4-isopropylpyridinio)methyldiphenylboron | 3 |
| (3-methylpyridinio)methyldiphenylboron | 3 |
| (3-isopropylimidazolinio)vinyldiphenylboron | 1 |
| (thiazolinio)methyldiphenylboron | 1 |
| (3-bromoisoquinolinio)methyldiphenylboron | 1 |
| (3-bromopyridinio)methyldiphenylboron | 1 |
| (4-phenylpyridinio)methyldiphenylboron | 1 |
| (4-cyanopyridinio)methyldiphenylboron | 1 |

[1]Artemia

EXAMPLE 2
Field Evaluation Of Marine Antifouling Activity Of Test Compounds (Raft Exposure)

In this evaluation, test compounds are dissolved in cyclohexanone. The solution is treated with vinylite (manufactured by Union Carbide) to obtain a final concentration of 26% in the dried coating. PVC boards (100×20×5 mm) are degreased by washing with ethanol and coated with the test formulation by brushing (2 coats). The total thickness of the test film is approximately 50 $\mu$M. The exact quantity of test compound on each board is determined by comparing the initial and final weights. The test sample boards are placed in a frame and immersed to a depth of 1M in the North Sea. The frames are suspended from the bottom of a raft and are intermittently raised to evaluate the surface fouling. The rating system used is shown below. The data are shown in Table II.

| RATING SCALE | |
| --- | --- |
| Rating | |
| 0 | No growth on the panel |
| 1 | 1–20% of the surface covered by animal foulers |
| 2 | 21–40% of the surface covered by animal foulers |
| 3 | 41–60% of the surface covered by animal foulers |
| 4 | 61–80% of the surface covered by animal foulers |
| 5 | 81–100% of the surface covered by animal foulers |

TABLE II

| | Weeks after treatment | | | | |
| --- | --- | --- | --- | --- | --- |
| Test Compound | 6 | 10 | 14 | 22 | 31 |
| (3-vinylimidazolinio)vinyldiphenylboron | 0 | 0 | 0 | 0 | 0 |
| (3-methylpyridinio)methyldiphenylboron | 0 | 0 | 1 | 2 | 1 |
| (3-isopropylpyridinio)vinyldiphenylboron | 0 | 1 | 5 | 5 | 4 |
| (thiazolinio)methyldiphenylboron | 0 | 0 | 1 | 2 | 2 |
| (3-bromoisoquinolinio)methyldiphenylboron | 0 | 3 | 5 | 5 | 5 |
| (3-bromopyridinio)methyldiphenylboron | 0 | 2 | 5 | 3* | 5 |
| (4-acetylpyridinio)methyldiphenylboron | 0 | 1 | 2 | 2* | 3 |
| (4-phenylpyridinio)methyldiphenylboron | 0 | 1 | 2 | 2 | 2 |
| (4-cyanopyridinio)methyldiphenylboron | 0 | 2 | 5 | 4 | 3 |
| (isoquinolinio)methyldiphenylboron | 0 | 1 | 4 | 5 | 5 |
| (4-t-butylpyridinio)methyldiphenylboron | 0 | 2 | 4 | 5 | 4 |
| (4-isopropylpyridinio)methyldiphenylboron | 0 | 0 | 1 | 1* | 1 |
| (5,6,7,8-tetrahydroisoquinolinio)methyldiphenylboron | 0 | 2 | 4 | 5* | 3 |
| Cuprous Oxide | 0 | 0 | 1 | 3 | 3 |
| Tri(n-butyl)Tin Oxide | 0 | 1 | 2 | 4 | 4 |
| Control | 4 | 5 | 5 | 5 | 5 |

*no barnacles

EXAMPLE 3

Evaluation Of Leaching Properties Of Test Compounds

Using essentially the same procedure described in Example 2, test panels (100×10×5 mm) are prepared. In this evaluation test panels are placed in 80 ml artificial sea water which is renewed weekly. At two week intervals, just after the sea water is refreshed, Artemia is added to each treatment. Three days after the addition of Artemia, the experiment is evaluated using the rating scale shown below. The activity of the test compound is expressed as the number of weeks during which the leaching is sufficient to cause a toxic effect, i.e. a rating of at least 2. The results are shown in Table III.

| Rating System | |
| --- | --- |
| Rating | |
| 1 | No activity, comparable to control |
| 2 | Toxic effect, but not 100% mortality (20–<80%) |
| 3 | Completely active (80–100% mortality) |

TABLE III

| Test Compound | Weeks Of Effective Leaching |
| --- | --- |
| (3-vinylimidazolinio)vinyldiphenylboron | >32 |
| (3-methylpyridinio)methyldiphenylboron | >32 |
| (3-isopropylpyridinio)vinyldiphenylboron | 0 |
| (thiazolinio)methyldiphenylboron | 24 |
| (3-bromoisoquinolinio)methyldiphenylboron | 0 |
| (3-bromopyridinio)methyldiphenylboron | 0 |
| (4-acetylpyridinio)methyldiphenylboron | 0 |
| (4-phenylpyridinio)methyldiphenylboron | >32 |
| (4-cyanopyridinio)methyldiphenylboron | 0 |
| (isoquinolinio)methyldiphenylboron | 20 |
| (4-t-butylpyridinio)methyldiphenylboron | >28 |
| (4-isopropylpyridinio)methyldiphenylboron | >28 |
| (5,6,7,8-tetrahydroisoquinolinio)methyldiphenylboron | 0 |
| Cuprous Oxide | 0 |
| Tri(n-butyl)Tin Oxide | 28 |
| Control | 0 |

We claim:

1. A method for controlling or combatting the attachment of a fouling organism to an underwater surface which comprises contacting said organism or the locus thereof with an antifouling effective amount of a compound of formula I

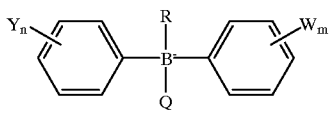

(I)

wherein R is $C_1$–$C_8$alkyl, $C_2$–$C_8$alkenyl or $C_2$–$C_8$alkynyl;

W and Y are each independently halogen, $C_1$–$C_8$alkyl or $C_1$–$C_8$haloalkyl;

m and n are each independently 0 or an integer of 1, 2 or 3;

Q is

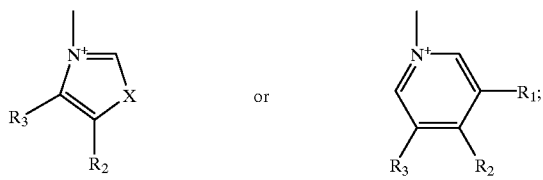

X is $NR_4$ or S;

$R_1$ is H, halogen, $C_1$–$C_8$alkyl, or $C_2$–$C_8$alkenyl;

$R_2$ and $R_3$ are each independently H, $C_1$–$C_8$alkyl, $C_1$–$C_8$haloalkyl, $C_1$–$C_8$alkoxy, $C_1$–$C_8$haloalkoxy, halogen, CN, $NO_2$, $COR_5$ or phenyl optionally substituted with one to three halogen or $NR_6R_7$ groups or $R_1$ and $R_2$ may be taken together with the atoms to which they are attached to form a saturated or unsaturated 6-membered carbocyclic ring optionally substituted with one to three halogen, $NO_2$, $C_1$–$C_4$alkyl or $C_1$–$C_4$alkoxy groups;

$R_4$ is $C_1$–$C_8$alkyl, $C_2$–$C_8$alkenyl or phenyl; and $R_5$, $R_6$ and $R_7$ are each independently H or $C_1$–$C_4$alkyl.

2. The method according to claim 1 wherein m and n are 0.

3. The method according to claim 1 wherein R is $C_1$–$C_4$alkyl or $C_2$–$C_4$alkenyl.

4. The method according to claim 1 wherein Q is

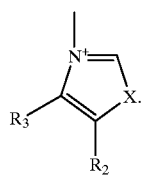

5. The method according to claim 1 wherein Q is

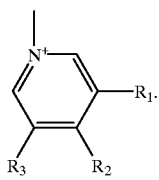

6. The method according to claim 1 wherein the fouling organism is selected from the group consisting of barnacles, zebra mussels, algae, diatoms, hydroids, bryozoa, ascidians, tubeworms and Asiatic clams.

7. The method according to claim 4 wherein the formula I compound is selected from the group consisting of (3-vinylimidazolinio)vinyldiphenylboron, (3-vinylimidazolinio)methyldiphenylboron, (3-isopropylimidazolinio)vinyldiphenylboron, and (thiazolinio)methyldiphenylboron.

8. The method according to claim 5 wherein the formula I compound is selected from the group consisting of (3-methylpyridinio)methyldiphenylboron, (4-phenylpyridinio)methyldiphenylboron, (4-t-butylpyridinio)methyldiphenylboron, (4-isopropylpyridinio)methyldiphenylboron, (3-bromopyridinio)methyldiphenylboron, (4-acetylpyridinio)methyldiphenylboron, (4-cyanopyridinio)methyldiphenylboron, (isoquinolinio)methyldiphenylboron, (3-bromoisoquinolinio)methyldiphenylboron and (5,6,7,8-tetrahydroisoquinolinio)methyldiphenylboron).

9. A method for protecting an aquatic structure against fouling by a marine or freshwater fouling organism which comprises applying onto or permeating into said structure an antifouling-effective amount of a compound of formula I

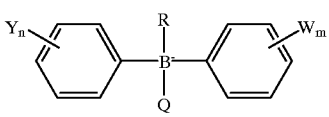

(I)

wherein R is $C_1$–$C_8$alkyl, $C_2$–$C_8$alkenyl or $C_2$–$C_8$alkynyl;

W and Y are each independently halogen, $C_1$–$C_8$alkyl or $C_1$–$C_8$haloalkyl;

m and n are each independently 0 or an integer of 1, 2 or 3;

Q is

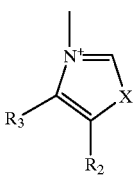 or 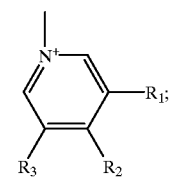

X is $NR_4$ or S;

$R_1$ is H, halogen, $C_1$–$C_8$alkyl, or $C_2$–$C_8$alkenyl;

$R_2$ and $R_3$ are each independently H, $C_1$–$C_8$alkyl, $C_1$–$C_8$haloalkyl, $C_1$–$C_8$alkoxy, $C_1$–$C_8$haloalkoxy, halogen, CN, $NO_2$, $COR_5$ or phenyl optionally substituted with one to three halogen or $NR_6R_7$ groups or $R_1$ and $R_2$ may be taken together with the atoms to which they are attached to form a saturated or unsaturated 6-membered carbocyclic ring optionally substituted with one to three halogen, $NO_2$, $C_1$–$C_4$alkyl or $C_1$–$C_4$alkoxy groups;

$R_4$ is $C_1$–$C_8$alkyl, $C_2$–$C_8$alkenyl or phenyl; and $R_5$, $R_6$ and $R_7$ are each independently H or $C_1$–$C_4$alkyl.

10. The method according to claim 9 wherein m and n are 0.

11. The method according to claim 9 wherein R is $C_1$–$C_4$alkyl or $C_2$–$C_4$alkenyl.

12. The method according to claim 9 wherein the aquatic structure is a fishnet, boat, ship, piling, pier, intake screen, cooling tower, pipeline or standpipe.

13. The method according to claim 9 wherein the marine or freshwater fouling organism is selected from the group consisting of barnacles, zebra mussels, algae, diatoms, hydroids, bryozoa, ascidians, tubeworms and Asiatic clams.

14. The method according to claim 11 wherein the formula I compound is selected from the group consisting of (3-vinylimidazolinio)vinyldiphenylboron, (3-vinylimidazolinio)methyldiphenylboron, (3-methylpyridinio)methyldiphenylboron, (4-phenylpyridinio)methyldiphenylboron, (4-t-butylpyridinio)methyldiphenylboron, (4-isopropylpyridinio)methyldiphenylboron, (3-isopropylimidazolinio)vinyldiphenylboron, (thiazolinio) methyldiphenylboron, (3-bromopyridinio) methyldiphenylboron, (4-acetylpyridinio) methyldiphenylboron, (4-cyanopyridinio) methyldiphenylboron, (isoquinolinio)methyldiphenylboron, (3-bromoisoquinolinio)methyldiphenylboron and 5,6,7,8-tetrahydroisoquinolinio)methyldiphenylboron.

* * * * *